United States Patent [19]

Radlowski

[11] Patent Number: 5,300,695
[45] Date of Patent: Apr. 5, 1994

[54] PROCESS FOR PREPARING ALCOHOLS

[75] Inventor: Cecelia A. Radlowski, Riverside, Ill.

[73] Assignee: Amoco Corporation, Chicago, Ill.

[21] Appl. No.: 986,384

[22] Filed: Dec. 7, 1992

[51] Int. Cl.$^5$ ................... C07C 41/06; C07C 29/34
[52] U.S. Cl. ................................. 568/697; 568/905
[58] Field of Search ........................ 568/905, 697

[56] References Cited

U.S. PATENT DOCUMENTS

| | | | |
|---|---|---|---|
| 1,755,692 | 4/1930 | Herrmann et al. | |
| 1,859,244 | 5/1932 | Patart | 518/713 |
| 1,992,480 | 2/1935 | Fuchs et al. | 260/156 |
| 2,050,788 | 8/1936 | Fuchs et al. | 260/156 |
| 2,861,110 | 11/1958 | Herzenberg et al. | 260/642 |
| 2,971,033 | 2/1961 | Farrar | 260/642 |
| 3,216,789 | 11/1965 | Breck et al. | 23/113 |
| 3,328,470 | 6/1967 | Poe | 260/642 |
| 4,104,320 | 8/1978 | Bernard et al. | 260/673 |
| 4,346,179 | 8/1982 | Sugier et al. | 518/707 |
| 4,513,100 | 4/1985 | Fattore et al. | 502/303 |
| 4,518,810 | 5/1985 | Matsuda et al. | 568/905 |
| 4,670,473 | 6/1987 | Walker et al. | 518/706 |
| 4,888,105 | 12/1989 | Huss, Jr. et al. | 208/137 |
| 5,028,312 | 7/1991 | Miller et al. | 208/138 |

FOREIGN PATENT DOCUMENTS

| | | | |
|---|---|---|---|
| 9104242 | 4/1991 | PCT Int'l Appl. | C07C 29/34 |
| 810981 | 2/1981 | South Africa | B01J C07C |
| 336811 | 10/1930 | United Kingdom | 568/902 |
| 478141 | 1/1938 | United Kingdom | 518/713 |

OTHER PUBLICATIONS

Langner, CA 96:202447u 1982.
"Condensation of Alcohols", Dvornikoff, et al., 1956, Journal unknown, pp. 540–542.
OCTAMIX: A New Technology For Mixed Alcohol Production, presented at AICHE Spring Meeting, Apr., 1986.
MAS Process: From Research To Commercialization, Paggini, et al., 1986, presented at AICHE Spring Meeting, Apr.

*Primary Examiner*—Howard T. Mars
*Attorney, Agent, or Firm*—Scott P. McDonald; Richard A. Kretchmer

[57] ABSTRACT

A process is provided in which an alcohol having X carbon atoms is reacted over an L-type zeolite catalyst to produce a higher molecular weight alcohol. In some embodiments, a first alcohol having X carbon atoms is condensed with a second alcohol having Y carbon atoms to produce a branched-chain alcohol having X+Y carbon atoms. Processes for making ethers useful as fuel oxygenates which incorporate the foregoing process steps also are disclosed.

17 Claims, 1 Drawing Sheet

PROCESS FOR PREPARING ALCOHOLS

FIELD OF THE INVENTION

This invention generally relates to processes for preparing oxygenated hydrocarbons. More specifically, the invention relates to L-type zeolite-catalyzed processes for producing higher molecular weight alcohols from relatively lower molecular weight alcohol feedstocks.

BACKGROUND OF THE INVENTION

The production of higher molecular weight alcohols from lower molecular weight feedstocks has long interested organic chemists. Such reactions are of much greater interest following the 1991 amendments to the Clean Air Act. These amendments require the blending of fuel oxygenates into gasoline in non-attainment regions of the United States. The required oxygenates are intended to lower carbon monoxide and ozone pollution contributions from internal combustion engine exhausts. Two compounds particularly suited for use as gasoline oxygenates are tertiary amyl methyl alcohol ether (TAME) and methyl tertiary butyl ether (MTBE).

Certain branched-chain alcohols such as isobutanol and isoamyl alcohol are useful as precursors for TAME and MTBE. Isobutanol is useful because it can be dehydrated to form isobutylene, which subsequently can be etherified with methanol to yield MTBE. Isoamyl alcohol, a common name for an isomeric mixture of 2-methyl-1-butanol and 3-methyl-1-butanol, can be reacted with methanol to yield TAME. The expected widespread use of fuel oxygenates requires that refiners develop efficient processes for producing these oxygenates and their precursors.

Guerbert syntheses typically have been used to prepare higher molecular weight branched-chain alcohols from lower molecular weight starting materials. A representative Guerbert synthesis is disclosed in U.S. Pat. No. 4,518,810. In this example, a single alcohol feedstock is batch-reacted over a copper-nickel alkaline catalyst at temperatures from about 200 to 250 degrees Centigrade to produce a dimerized alcohol product. The product alcohol is a branched-chain dimer alcohol in which a dehydration reaction has removed the hydroxyl group from the alpha carbon of a first alcohol molecule and a hydrogen atom from a beta methylene carbon of a second alcohol molecule. The resultant alcohol has a carbon—carbon bond located between the alpha carbon of the first alcohol's carbon chain and the beta carbon of the second alcohol's carbon chain.

In addition to the dimerization reaction discussed above, Guerbert syntheses also have been used to condense together two different alcohols. In this case, at least one of the two alcohols must contain a dehydratable carbon atom at the beta position. An example of this type of reaction is that disclosed in U.S. Pat. No. 2,050,788, in which a mixture of ethyl and methyl alcohol and a stoichiometric excess of hydrogen is condensed over a MgO/CuO catalyst at temperatures between about 200 and 350 degrees Centigrade to provide a mixture of higher molecular weight alcohols.

While the foregoing Guerbert synthesis reactions can, under certain conditions, provide useful yields of certain higher molecular weight alcohols, the catalysts employed are believed to be subject to scintering under regeneration conditions and therefore not well-suited to the cyclic operation common in catalytic refinery operations. Refiners therefore continue to seek improved processes for producing fuel oxygenates and oxygenate precursors. Preferably, these processes should employ modern, commercially-available, easily-regenerated catalysts.

SUMMARY OF THE INVENTION

The present invention is a process for preparing relatively higher molecular weight alcohols by reacting relatively lower molecular weight primary linear alcohol feedstocks over an L-type zeolite catalyst.

In the broadest embodiment of the invention, a process for producing higher molecular weight alcohols is disclosed wherein one or more lower molecular weight alcohols are contacted with an L-type zeolite under dehydration conditions. In some of these embodiments, the catalyst employed is a potassium form of L-type zeolite. In other embodiments, the L-type zeolite can be a cation-exchanged form that can have one or more catalytic metals such as platinum or palladium deposited thereon.

In other embodiments of the invention, a method for producing higher molecular weight alcohols is disclosed in which two different alcohols having X and Y carbon atoms, respectively, are contacted with an L-type zeolite catalyst under dehydration conditions to produce a branched-chain alcohol having $X+Y$ carbon atoms. In some of these embodiments, the use of particular feedstock combinations such as 1-propanol and methanol provides for higher yields of isobutanol than when other multi-alcohol feedstocks such as a methanol/ethanol feedstock are employed.

In still other embodiments of the invention, a process for making ether fuel components is disclosed which comprises the steps of contacting a first alcohol having X carbon atoms and a second alcohol having Y carbon atoms over an L-type zeolite catalyst under dehydration conditions to produce a branched-chain product alcohol having at least $X+Y$ carbon atoms wherein $X+Y$ is equal to 6 or less, dehydrating the alcohol to form an olefin, and reacting the olefin with a third alcohol having Z carbon atoms wherein Z can be 1, 2 or 3 to form a dialkyl ether of the form $R_1OR_2$ wherein $R_1$ is an alkyl group having at least $X+Y$ carbon atoms and wherein $R_2$ is an alkyl group having Z carbon atoms. In some of these embodiments, the alcohol for the initial alcohol synthesis and/or the etherification is provided by reacting a syngas feedstock to produce the required alcohol.

Each of these embodiments provides a useful refinery process because the use of an L-type zeolite-catalyzed alcohol synthesis process facilitates the regeneration and reuse of the process catalyst while at the same time producing commercially-significant yields of the desired oxygenate or oxygenate precursor.

Other advantages of the invention will be apparent to those skilled in the art from the following detailed description and the appended claims.

DETAILED DESCRIPTION OF THE INVENTION

Figure 1:
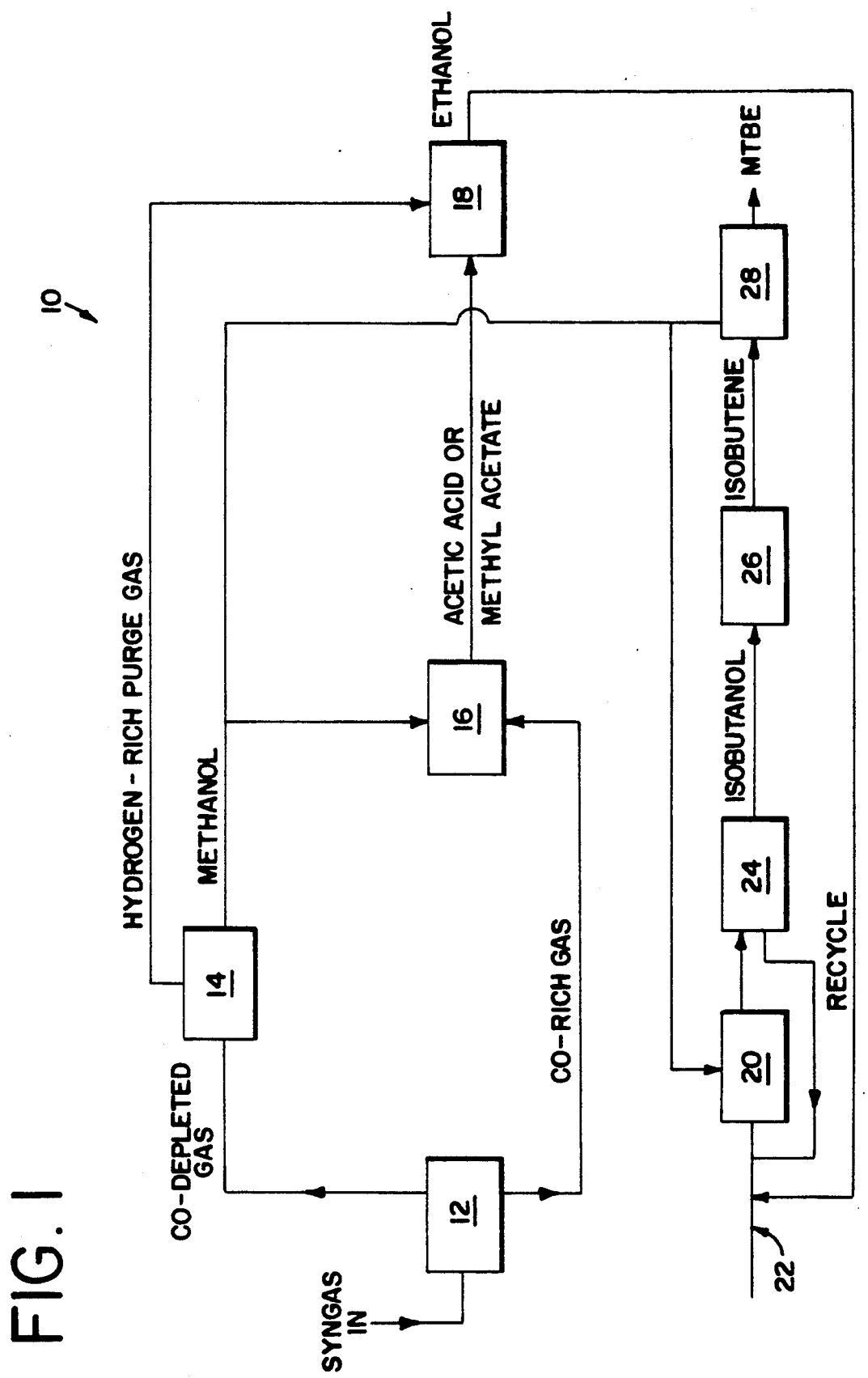
FIG. 1 is a flow diagram of a process for producing methyl tertiary-butyl ether in accordance with the present invention.

In each embodiment of the invention discussed below, primary linear alcohol feedstocks are reacted over an L-type zeolite catalyst to produce relatively higher molecular weight alcohols, many of which are suitable for use as fuel oxygenates or oxygenate precursors. As the following discussion and Examples illustrate, the invention can be tailored to provide relatively high yields of certain alcohols given careful selection of the alcohol feedstocks and reaction conditions.

The alcohol feedstocks most useful in the invention are primary linear alcohols having between 1 and 20 carbon atoms. In some cases, it may be desirable to use a single alcohol feedstock which will at first react with itself to form product dimer alcohols. These product dimers can be used as is or allowed to react with additional alcohol feedstock or similar dimers to form still higher molecular weight alcohols. For example, ethanol may be dehydrated over an L-type zeolite catalyst to produce n-butanol, which may be used to manufacture TAME or blended directly into fuel.

Where greater selectivity for a particular product alcohol is desired, two different primary linear alcohols having X and Y carbon atoms, respectively, can be condensed to produce a desired primary alcohol product having X+Y carbon atoms. Reacting selected alcohol feedstocks in this manner typically can result in a selectivity for the desired alcohol of greater than twenty-five percent, particularly where the reaction is conducted at weight hourly space velocities greater than 1 gram of alcohol per one gram of catalyst per hour. Choosing the appropriate starting alcohol feed components allows particular isomers of the dominant higher alcohol to be tailored as desired. For example, ethanol can be reacted in the process to produce n-butanol, while if methanol and n-propanol are chosen as feedstocks, isobutanol is the dominant alcohol produced in the reaction.

As the Examples herein demonstrate, the process is believed to be particularly suited to syntheses where it is desired to form a carbon—carbon bond between the alpha carbon atom of a first linear primary alcohol feedstock and the beta carbon atom of a second linear primary alcohol feedstock to produce a branched-chain primary alcohol.

The process also may be performed using a mixture of three or more alcohols as a feedstock. For example, a mixture of methanol, ethanol and n-propanol may be reacted over an L-type zeolite to produce isobutanol. In this case, selectivity for isobutanol should be expected to be somewhat less than if the isobutanol were produced from a mixture of methanol and n-propanol.

Of particular interest are those reactions yielding intermediates for the production of TAME or MTBE. These reactions include the reaction of methanol and a stoichiometric excess of ethanol to produce n-propanol, an isobutanol precursor; the reaction of n-propanol with methanol to produce isobutanol, which can in turn be dehydrated and reacted with additional methanol to produce MTBE; the reaction of two moles of ethanol to yield one mole of n-butanol; and the dehydration of methanol and n-butanol to yield 2-methyl-1-butanol and the dehydration of ethanol and n-propanol to yield 3-methyl-1-butanol, both of which are TAME precursors.

If available, the feed also may contain as reactants supplemental feed components such as aldehydes, ethers or ketones, each preferably having carbon atom chains containing the same number of carbon atoms as at least one of the alcohol feedstocks. While supplemental reactants having carbon atom chains with more or less carbon atoms than the primary linear alcohol feedstocks may be used, use of these supplemental feedstocks is likely to diminish the selectivity of the reaction for the desired product.

Supplemental feed components particularly useful for producing gasoline oxygenates include aldehydes such as formaldehyde, acetaldehyde and propionaldehyde; ethers such as dimethyl-, diethyl- and dipropyl-ether; carboxylic acids such as acetic acid; and ketones such as acetone and methyl ethyl ketone. Of these supplemental feedstock components, ketones and aldehydes are preferred as they are believed either to be or to readily form an important intermediate in the production of the desired higher molecular weight alcohol. The ether and carboxylic acid reactants generally can be present in the feedstock in an amount of 0 to about 25 mole percent, and preferably no more than about 0 to 10 percent. Aldehyde and ketone components may comprise up to 90 percent of the feedstock.

If an olefin having the same carbon number as an alcohol feedstock is available, the olefin may be used in part to supplement that alcohol feedstock. This could be beneficial where an olefin is economically available from other, nearby process units. Olefin feedstock content should not exceed about ten weight percent of the feed for any particular carbon number feedstock to minimize olefin polymerization within the reactor.

The feed also can contain up to about 50 percent of one or more gases such as methane, nitrogen, hydrogen, carbon monoxide and carbon dioxide. While the use of one of these gaseous feed components is not required, such a gaseous component can function as a carrier gas to carry reactants and products through the catalytic reactor system as discussed below.

L-type zeolite catalysts useful in the invention are a sub-group of zeolitic catalysts. The term "zeolite" generally refers to a particular group of hydrated, crystalline metal aluminosilicates. These zeolites exhibit an open three-dimensional framework of $SiO_4$ and $AlO_4$ tetrahedra in which the tetrahedra are crosslinked by the sharing of oxygen atoms. In the framework, the ratio of oxygen atoms to the total of aluminum and silicon atoms is equal to 2. The framework exhibits a negative electrovalence which typically is balanced by the inclusion of cations within the crystal such as metals, alkali metals, alkaline earth metals or hydrogen.

The L-type zeolites useful in the invention are those zeolites containing mole ratios of oxides in accordance with the following formula:

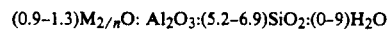

$$(0.9-1.3)M_{2/n}O: Al_2O_3:(5.2-6.9)SiO_2:(0-9)H_2O$$

wherein "M" designates at least one exchangeable cation and "n" represents the valence of "M". The crystal structure these L-type zeolites are based on is the 18 tetrahydra unit known as the "epsilon-cage", with the main structural unit of the crystal being the double six ring (D6R) unit. The crystal structure contains alternating epsilon-cage/D6R/epsilon-cage units crosslinked to other identical units by oxygen bridges. This arrangement gives rise to planar 12 member rings that provide for parallel one-dimensional channels having a free diameter of about 7.1 Angstroms.

As used herein, the term L-type zeolite includes any cation-containing form of L-type zeolite. These L-type zeolites can contain metallic cations such as barium, calcium, cerium, lithium, magnesium, potassium, sodium, strontium, and zinc as well as non-metallic cations like hydronium and ammonium ions which may be replaced by other exchangeable cations without causing a substantial alteration of the basic crystal structure of the L-type zeolite. L-type zeolites and methods for their preparation are described in U.S. Pat. No. 3,216,789, which is hereby incorporated by reference.

Potassium L-type zeolites have been found to be particularly suitable for use in the invention. The term KL zeolite as used herein refers to these L-type zeolites in which the principal cation M incorporated in the zeolite is potassium. As used in this application, a KL zeolite is one that has not been significantly cation-exchanged or impregnated with another metal unless the term KL zeolite is preceded by a modifier such as "barium-exchanged" or "platinum-impregnated" or the zeolite explicitly is referred to as a "Ba KL zeolite" or a "Pt KL zeolite."

L-type zeolites useful in the invention can be modified by the incorporation of beneficial amounts of Group VIII metals such as platinum, ruthenium, rhodium, and/or palladium or a Group IB metal such as copper or silver. In general, these metal-impregnated catalysts will contain no more than about 5 weight percent of the metal and preferably will contain between about 0.5 to about 1.5 weight percent of the metal. The catalytic metal component may be added to the L-type zeolite support by any of several means known in the art including coprecipitation, impregnation or mixed oxide intimate blending. Iron or cobalt should not be used, however, as these metals are believed to promote undesired hydrocarbon formation under the process conditions disclosed herein. The Periodic Table group designations used herein refer to those found in the Periodic Table on page 874 of Webster's Ninth New Collegiate Dictionary, published by Merriam-Webster, Incorporated (1991).

It should be noted that while L-type zeolites have been found to be particularly useful for higher alcohol synthesis, other zeolites known in the art may also be useful in various cation-exchanged and/or impregnated forms similar to those discussed herein.

The reaction should be conducted over the L-type zeolite catalyst under suitable dehydration conditions. These dehydration conditions include temperatures between about 200 and 500 degrees Centigrade, operating pressures from subambient to about 2,000 psig, and weight hourly space velocities ranging between about 0.2–300 $hr^{-1}$. Preferred dehydration conditions include temperatures between 370 and 425 degrees Centigrade, pressures between 150 and 600 psig, and weight hourly space velocities between 2 and 20 $hr^{-1}$. When methanol is used as a feedstock, higher operating temperatures should be avoided as the methanol tends to decompose at high operating temperatures. The reaction preferably is conducted at weight hourly space velocities exceeding 1 gram of alcohol per gram of catalyst per hour as these space velocities increase weight selectivity for the desired product $alcohol$. As used herein weight percent selectivity refers to the percent of the dominant alcohol feedstock converted to a specific product alcohol. Although relatively low space velocities increase lower alcohol feedstock conversion, increases in carbon oxide and light hydrocarbon production make such space velocities less preferred.

Reactors used in the process can be a fixed bed, ebullated bed, fluidized bed, or other type of vapor phase process or reactor. The reactor preferably is quartz- or copper-lined to minimize the production of hydrocarbons from syngas produced in situ when methanol is used as a feedstock. When non-methanol feedstocks are employed, stainless steel can be used to construct the reactor.

As discussed above, use of a carrier gas mixed with the feed can be advantageous but is not required. Gases providing for a reducing atmosphere such as hydrogen, a hydrocarbon or syngas as well as inert gases such as nitrogen, helium, argon may be used to provide flow through the reactor. The use of a hydrogen carrier gas in the process can improve selectivity and, if use, can be employed in a hydrogen/feed molar ratio of from about 20:1 to about 1:1, and more preferably, from about from 10:1 to about 1:1. The use of hydrogen may also benefit the process by mitigating the decomposition of methanol to carbon monoxide and hydrogen.

If a carrier gas is not used, the alcohol feedstocks may be pumped into the reactor as liquids. This provides the added advantage that a carrier gas need not be separated from the reaction products.

The catalyst may be used in the reactor neat, or can be admixed with a diluent such as zirconia, titania, boria, alumina, silica, or a carbonaceous material such as charcoal. Such diluents need not be completely inert and it appears that the use of charcoal as a diluent improves at least certain of the condensation reactions described herein. The diluent and L-type zeolite catalyst can be admixed in proportions of about 100 weight percent catalyst and no diluent to about 10 weight percent catalyst and about 90 weight percent diluent. More preferably, the proportions may vary between catalyst to diluent ratios of 1:4 and 4:1. While the use of a diluent such as charcoal is not required by the slightly exothermic nature of the reaction, such diluents provide for better catalyst dispersal and gas flow through the reactor.

After the feed is contacted with the catalyst, the product effluent will contain a mixture of alcohols and other oxygenated hydrocarbons, including at least one of which will be a desired product alcohol which is of higher molecular weight than any of the starting alcohols. These products can be separated by distillation or other means well-known in the art.

The stoichiometric ratio of alcohols in multi-alcohol feedstocks significantly affects the yields of various product alcohols. For example, when methanol and ethanol were used as co-feedstocks with methanol present in excess, the reaction predominantly yielded n-propanol and isobutanol. On the other hand, where ethanol was present in excess, the reaction yields relatively higher concentrations of n-butanol, probably from the competing self-condensation of ethanol. Where it is desired to add a methyl group to a primary alcohol, methanol can be present in the range of about 2 to 5 times the molar amount of the heavier alcohol feedstock, with a ratio of 2.5 to 4 being preferred. Other useful molar feed ratios for alcohols and aldehydes are disclosed in the Examples below. Where methanol is one of the selected feedstocks, it may be preferred to feed methanol to the reactor in a stoichiometric excess to minimize dimerization of a more expensive, higher molecular weight alcohol.

In a first preferred embodiment of the invention, methanol and ethanol are reacted in a 3.3:1 molar ratio over a KL zeolite. The major condensable products of this reaction are water and $C_{2+}$ alcohols, with isobutanol the predominant product alcohol. Other alcohols which may be present in the product effluent in significant quantities include 1-propanol, 1-butanol and 2-methyl-1-butanol. The product effluent also can contain lesser amounts of corresponding $C_{2+}$ aldehydes, esters and acetals, as well as gaseous products such as carbon monoxide, carbon dioxide, methane and lesser amounts of $C_{2+}$ gaseous hydrocarbons. The reaction is believed to proceed by the formation of n-propanol from methanol and ethanol, with the n-propanol being further alkylated by the excess methanol to form isobutanol.

In a second preferred embodiment of the invention, methanol and 1-propanol in a 3.3:1 molar ratio are contacted with a KL zeolite to produce relatively high yields of isobutanol. Selectivity to isobutanol is greater in this case than when methanol and 1-propanol are used as feedstocks. The higher selectivity to isobutanol is believed to be attributable to the fact that the n-propanol need not be formed as an intermediate in this scheme.

A particularly useful process which may be carried out employing the L-type zeolite catalyzed reaction is the production of MTBE. In one embodiment of this process, methanol and 1-propanol are contacted with an L-type zeolite catalyst to produce isobutanol. The isobutanol then is separated from the mixture, dehydrated to form isobutylene and reacted with additional methanol to form MTBE. This is exemplary of the larger class of reactions in which an ether fuel component can be produced by contacting a first alcohol having X carbon atoms and a second alcohol having Y carbon atoms over an L-type zeolite catalyst under dehydration conditions to produce a product alcohol having at least $X+Y$ carbon atoms wherein $X+Y$ is equal to 6 or less, dehydrating the alcohol to form an olefin, and then reacting the olefin with a third alcohol having Z carbon atoms wherein Z can be 1, 2 or 3 to form a dialkyl ether of the form $R_1OR_2$, wherein $R_1$ is an alkyl group having at least $X+Y$ carbon atoms and wherein $R_2$ is an alkyl group having Z atoms.

Dehydration reactions suitable for converting alcohols to olefins in the above-described syntheses are well-known in the art. Suitable schemes include dehydrating liquid alcohols in 20 to 95 percent concentrations of mineral acids such as sulfuric or phosphoric acid at temperatures up to about 100 degrees Centigrade. Other more preferred schemes include the dehydration of vaporized alcohol over alumina or solid acid or other catalysts at temperatures ranging from the boiling point of the alcohol to about 400 degrees Centigrade.

Etherification reactions for converting olefins to the above-described ethers are also well known in the art. Most of these reactions involve reacting iso-olefin and alcohol vapors over a fixed bed of an etherification catalyst such as a medium pore zeolite catalyst or a solid acid resin catalyst. Representative modern processes useful for forming olefins by dehydration and/or etherifying an olefin/alcohol mixture include U.S. Pat. Nos. 5,015,782; 4,950,803; 4,847,431; and 4,806,695, the disclosures of which are hereby incorporated by reference.

While the foregoing processes can employ alcohol feedstocks from any source, a processing scheme of particular interest is one using synthesis gas as a significant source of carbon. An exemplary process for producing MTBE in this manner is shown in FIG. 1.

FIG. 1 illustrates an integrated process 10 for producing MTBE from synthesis gas. In process 10, the hydrogen/carbon monoxide synthesis gas mixture enters a gas separation unit 12. Unit 12 partitions the syngas mixture into a CO-rich feedstream and a CO-depleted feedstream. The CO-rich feedstream is fed to a methanol synthesis unit 14 where any of several commercially-available technologies can be used to convert the synthesis gas feedstream to methanol.

A portion of the methanol-rich product stream from synthesis unit 14 is fed to a carbonylation unit 16 along with the CO-rich syngas stream from unit 12. Carbonylation unit 16 converts these feedstocks to acetic acid and/or methyl acetate, which can then be fed to a hydrogenolysis unit 18 along with a hydrogen-rich purge gas from synthesis unit 14 to produce an ethanol-rich product.

Methanol from synthesis unit 14 also is fed to a catalytic condensation unit 20 where it reacts over an L-type zeolite catalyst with ethanol-rich feedstock from unit 18. Alternatively, ethanol or propanol can be introduced through a feedline 22 into condensation unit 20. Condensed product from condensation unit 20 then is directed to a separation unit 24, where isobutanol is separated from lower alcohols present in the product stream. The lower alcohols are recycled to condensation unit 20, while isobutanol is fed to a dehydration unit 26 where the isobutanol is converted to isobutene. The isobutene is then reacted in MTBE unit 28 with methanol from synthesis unit 14 to produce MTBE for gasoline blending.

The foregoing detailed descriptions are given to foster an understanding of the invention and in no way limit the invention, as modifications within the scope of the invention will be apparent to those skilled in the art.

The invention now is described in further detail in connection with the following Examples which illustrate various embodiments of the invention.

EXAMPLES

Each of the following processes was evaluated in a fixed-bed, continuous, downflow stainless steel reactor. The reactor was equipped with either a quartz or a copper liner. The catalyst was ground to 12/20 mesh size and physically mixed with charcoal bed diluent of the same mesh size. Typically, 5 cc of catalyst was mixed with 27 cc of charcoal supplied by Sargent-Welch. The catalyst bed was centered in the reactor with baffles of inert alumina balls both above and below the bed for heat transfer. The alumina balls were kept at a lower temperature than the catalyst bed. The reactor was pressurized with helium unless otherwise noted and the catalyst was brought to reaction temperature in flowing helium, at which time the alcohol was introduced via a Ruska pump.

Liquid product was condensed at pressure in a chilled receiving vessel. The products were analyzed by three gas chromatographic systems:

(1) $CO$, $CO_2$ and $CH_4$ were analyzed using a Hewlett-Packard on-line 5730 gas chromatograph equipped with a thermal conductivity detector and a Chromosorb 106 packed column. Analysis was accomplished by comparing results to an external standard containing known quantities of $CO$, $CO_2$ and $CH_4$.

(2) The non-condensible light gases ($C_1$-$C_6$ hydrocarbons), were analyzed off-line using a flame ionization detector and a six foot N-octane Porosil C column. The peaks were identified and measured by matching retention times with an external standard containing a known $C_1$-$C_6$ hydrocarbon mixture. Relative weight percentages of the various light gases were calculated by comparing peaks from the reaction mixture to peaks obtained from the standard.

(3) The condensible materials were collected in a bomb and analyzed with a flame ionization detector equipped with a 30 meter capillary column of fused silica containing an RSL 160 liquid phase. Peaks were identified by matching retention times of known alcohols, aldehydes, esters, ketones, olefins and paraffins. Many of the smaller peaks were not identified. The results expressed below are given in relative weight percents unless otherwise indicated.

The condensible liquids also were measured on a Hewlett-Packard 5730 gas chromatograph equipped with a thermal conductivity detector. A 6 ft.×⅛ in. Poropak QS column, 80/100 mesh particles, was used. This system gave semi-quantitative results for water, $C_1$–$C_5$ alcohols, and some lower molecular weight aldehydes, ketones, and esters.

Four different catalysts were used in the following Examples.

Catalyst A was TSZ-500-KOA Zeolite L, a large pore potassium L-zeolite available from Tosoh USA Inc. of Atlanta, Ga. This L-zeolyte typically contains about 64.6 weight percent $SiO_2$, about 7.8 weight percent $Al_2O_3$, about 0.15 weight percent $Na_2O$, and about 15.9 weight percent $K_2O$, all weights on a dry basis. The material was approximately 80 percent crystalline L-zeolite relative to amorphous $SiO_2$-$Al_2O_3$.

Catalyst B was a barium-exchanged potassium L-type zeolite prepared in the following manner. A round-bottom flask equipped with a water-cooled condenser and stirrer was charged with 18.79 grams of $Ba(NO_3)_2$ dissolved in 225 ml $H_2O$. 75 grams of Catalyst A was added to the flask. The mixture was heated at 90° C. with stirring for 3 hours and then filtered. The exchanged zeolite was then reslurried in 225 mls of hot water, stirred for an additional hour and refiltered. The filtered zeolite cake was allowed to dry overnight on the bench top. The dried filter cake then was transferred to a vacuum oven and dried at 84° C. The dried catalyst was reslurried two additional times in 225 ml of water for 30 to 60 minutes at 90° C. and dried.

Catalyst C was a palladium-impregnated variant of Catalyst B prepared by depositing 7.5 ml of Pd $(NH_3)_4(NO_3)_2$ solution (4.1% Pd) on 25 grams of Catalyst B. The impregnated catalyst was allowed to dry on the bench top for 72 hours. The dried catalyst contained approximately 1.0 weight percent palladium by weight.

Catalyst D was a platinum-impregnated potassium L-zeolite prepared by slurrying 100 grams of barium nitrate with 200 grams of a potassium L-zeolite available from the Union Carbide Company as ELZ-L in 600 mls of distilled water. The slurry was stirred at 90° C. for 3 hours. The barium-exchanged catalyst was filtered and washed by reslurrying the catalyst in 600 mls of distilled water and stirring at 90° C. for 30 minutes. The washed catalyst was dried overnight at 120° C. Platinum was then impregnated on 20 grams of the barium-exchanged zeolite by depositing 13 ml of a solution containing 0.20 grams of platinum as Pt $(NH_3)_4(NO_3)_2$. The impregnated catalyst was dried overnight at 120° C. The dried catalyst contained approximately 1.0 weight percent platinum by weight.

EXAMPLE 1

This example demonstrates the KL zeolite-catalyzed synthesis of isobutanol from methanol and ethanol and the effect of weight hourly space velocity on reaction product distribution. In this example, a 3.3 Molar: 1 Molar methanol/ethanol feedstock was reacted over 2.6 grams of Catalyst A and about 27 cubic centimeters of charcoal at four different weight hourly space velocities as summarized in Table 1. A helium carrier gas was used to provide flow through the copper-lined reactor. As can be seen by comparing the product distributions and operating conditions presented in Table 1, the larger weight hourly space velocities surprisingly provided for greater selectivity for isobutanol than did the lesser space velocities. It should also be noted that the reactions run at the lesser space velocities converted greater amounts of methanol and ethanol to undesired products such as carbon oxides and $C_2+$ hydrocarbons.

TABLE 1

| Reaction Conditions | | | | |
|---|---|---|---|---|
| Temperature, Centigrade | 425 | 425 | 425 | 425 |
| Pressure, psig | 150 | 150 | 150 | 150 |
| Helium Flow, (cc/hr) | 2266 | 2266 | 2266 | 2266 |
| MeOH/EtOH Feed (cc/hr) | 10.28 | 5.10 | 2.58 | 1.02 |
| WHSV (g Alc./g cat/hr) | 3.12 | 1.55 | 0.78 | 0.31 |
| Wt % Methanol Converted | 20.08 | 27.98 | 32.16 | 42.44 |
| Wt % Ethanol Converted | 83.98 | 92.25 | 96.40 | 100.00 |
| Wt % Selectivity of Products (water-free) | | | | |
| n-$C_3H_7OH$ | 7.90 | 0.00 | 1.28 | 0.00 |
| i-$C_4H_9OH$ | 36.28 | 31.55 | 26.00 | 7.79 |
| n-$C_4H_9OH$ | 0.00 | 0.00 | 0.00 | 0.00 |
| t-$C_4H_9OH$ | 5.09 | 0.00 | 6.11 | 1.99 |
| CO | 11.16 | 11.80 | 15.31 | 20.40 |
| $CO_2$ | 4.68 | 5.95 | 10.84 | 15.86 |
| $CH_4$ | 6.03 | 5.54 | 6.50 | 8.19 |
| $C_2+$ Hydrocarbons | 27.12 | 24.06 | 24.82 | 45.76 |
| Acetaldehyde | 0.00 | 0.00 | 0.00 | 0.00 |
| Methyl Formate | 0.00 | 0.00 | 0.00 | 0.00 |
| Isopropanol | 0.00 | 0.00 | 0.00 | 0.00 |
| Methyl Acetate | 0.00 | 0.78 | 0.23 | 0.00 |
| Ethyl Acetate | 0.00 | 0.00 | 0.00 | 0.00 |
| 1-Pentanol | 0.00 | 0.00 | 0.00 | 0.00 |
| Hexanol+ | 0.00 | 0.00 | 0.00 | 0.00 |
| Other | 1.75 | 20.31 | 8.91 | 0.00 |

EXAMPLE 2

This example demonstrates the effect of alcohol feedstock choice on selectivity for isobutanol. In each run, an alcohol-containing feedstock was reacted over 2.6 grams of Catalyst A and about 27 cubic centimeters of charcoal. In Runs 1 and 2, a 3.3M:1M methanol/ethanol mixture was fed into the reactor using a helium carrier gas. In Runs 3 and 4, a 3.3M:1M methanol/isopropanol mixture was fed into the reactor with a helium carrier gas. In Run 5, a 100 percent ethanol feedstock was fed into the reactor with a helium carrier gas, while in Runs 6 and 7, a 3M:1M ethanol/acetaldehyde mixture was fed into the reactor with a carrier gas comprising 95.1 percent helium and 4.9 percent propene. The experimental conditions and product distributions from these runs are presented in Table 2.

TABLE 2

| | Run 1 | Run 2 | Run 3 | Run 4 | Run 5 | Run 6 | Run 7 |
|---|---|---|---|---|---|---|---|
| Alcohol Feed | 3.3 M MeOH/ EtOH | 3.3 M MeOH/ EtOH | 3.3 M MeOH/ PrOH | 3.3 M MeOH/ PrOH | Run 5 100% EtOH | 3M EtOH/ Acetaldehyde | 3M EtOH Acetaldehyde |
| Temperature, C. | 425 | 425 | 425 | 425 | 425 | 425 | 425 |

TABLE 2-continued

| Alcohol Feed | Run 1<br>3.3 M MeOH/<br>EtOH | Run 2<br>3.3 M MeOH/<br>EtOH | Run 3<br>3.3 M MeOH/<br>PrOH | Run 4<br>3.3 M MeOH/<br>PrOH | Run 5<br>100% EtOH | Run 6<br>3M EtOH/<br>Acetaldehyde | Run 7<br>3M EtOH<br>Acetaldehyde |
|---|---|---|---|---|---|---|---|
| Pressure, psig | 565 | 565 | 565 | 565 | 565 | 565 | 565 |
| Diluent Gas Flow, (cc/hr) | 850 | 850 | 850 | 850 | 2549 | 2549 | 2549 |
| Alcohol Feed (cc/hr) | 9.80 | 5.10 | 10.04 | 5.15 | 5.23 | 5.4 | 17.93 |
| Carrier Gas | He | He | He | He | 4.9% propene in helium | 4.9% propene in helium | 4.9% propene in helium |
| WHSV (g. alc./g. cat./hr) | 2.98 | 1.55 | 3.05 | 1.56 | 1.59 | 1.64 | 5.45 |
| Wt % Methanol Converted | 23.21 | 26.35 | 23.40 | 33.10 | 0 | 0 | 0 |
| Wt % Ethanol Converted | 68.64 | 70.89 | 0 | 0 | 46.33 | 3.53 | 7.33 |
| Wt % Propanol Converted | 0 | 0 | 64.70 | 73.26 | 0 | 0 | 0 |
| Wt % Propene Converted | 0 | 0 | 0 | 0 | 25.8 | 17.1 | 58.6 |
| Wt % Acetaldehyde Converted | 0 | 0 | 0 | 0 | 0 | 3.7 | 10.5 |
| Wt % Selectivity (Water-Free) | | | | | | | |
| n-$C_3H_7OH$ | 0.00 | 6.87 | 0.00 | 0.00 | 0.00 | 0.00 | 0.00 |
| i-$C_4H_9OH$ | 31.91 | 13.92 | 39.56 | 29.84 | 0.00 | 0.00 | 6.49 |
| n-$C_4H_9OH$ | 0.00 | 0.00 | 0.00 | 0.00 | 8.93 | 11.35 | 22.85 |
| t-$C_4H_9OH$ | 0.00 | 0.00 | 14.79 | 13.82 | 0.00 | 0.00 | 0.00 |
| CO | 19.42 | 27.33 | 19.22 | 23.70 | 8.18 | 15.08 | 11.30 |
| $CO_2$ | 12.56 | 19.82 | 11.32 | 17.30 | 17.15 | 15.36 | 5.49 |
| $CH_4$ | 6.43 | 5.50 | 2.39 | 3.21 | 6.76 | 7.79 | 4.96 |
| $C_2+$ Hydrocarbons | 12.41 | 14.45 | 5.74 | 10.25 | 9.51 | 13.37 | 7.79 |
| Acetaldehyde | 0.00 | 0.00 | 0.00 | 0.00 | 11.71 | | |
| Methyl Formate | 0.00 | 0.00 | 0.00 | 0.00 | 0.00 | 0.00 | 0.00 |
| Isopropanol | 0.00 | 0.00 | 0.00 | 0.00 | unknown | 0.00 | 0.00 |
| Methyl Acetate | 0.00 | 0.00 | 0.00 | 0.00 | 0.00 | 0.00 | 0.00 |
| Ethyl Acetate | 0.00 | 0.00 | 0.00 | 0.00 | 2.35 | 4.65 | 6.87 |
| 1-Pentanol | 0.00 | 0.00 | 0.00 | 0.00 | 5.90 | 5.13 | 4.34 |
| Hexanol+ | 0.00 | 0.00 | 0.00 | 0.00 | 0.00 | 0.00 | 0.00 |
| Other | 17.20 | 11.99 | 6.78 | 1.96 | 29.57 | 26.79 | 30.06 |

As can be seen by comparing Runs 1-4, the methanol/propanol feedstock typically provided for a higher selectivity to isobutanol. While not wishing to be bound to any particular theory, this may be attributable to propanol being an important intermediate in the synthesis of isobutanol from ethanol and methanol.

As can be seen from Runs 5-7, the use of C2 aldehyde and alcohol feedstocks alone or in combination with small amounts of propene tended to produce primarily normal butanol rather than the desired isobutanol product. These later synthesis routes may still be useful in the production of oxygenates, however, as n-butanol can be condensed with methanol in the same or a similar process to produce isoamyl alcohol, a precursor for the oxygenate tertiary amyl methyl ether (TAME).

EXAMPLE 3

This Example demonstrates the synthesis of isobutanol from methanol/ethanol and methanol/propanol feedstocks using palladium-impregnated Catalyst C. In Run 1, a 3.3M:1M methanol/ethanol feedstock was reacted over 3.23 grams of Catalyst C and about 27 cubic centimeters of charcoal. In Run 2, a 3.4M:1M methanol/propanol feedstock was reacted over 3.23 grams of Catalyst C and about 27 cubic centimeters of charcoal. In each run, a helium carrier gas was used to provide flow through the copperlined reactor. The experimental conditions and product distributions are summarized in Table 3.

TABLE 3

| Alcohol Feed | Run 1<br>3.3 MMeOH/EtOH | Run 2<br>3.4 MMeOH/PrOH |
|---|---|---|
| Temperature, Centigrade | 425 | 425 |
| Pressure, psig | 150 | 150 |
| Diluent Gas Flow, (cc/hr) | 2800 | 2800 |
| MeOH/EtOH (cc/hr) | 16.54 | 16.56 |
| WHSV (g Alc./g cat/hr) | 4.05 | 4.05 |
| Wt % Methanol Converted | 10.41 | 10.92 |
| Wt % Ethanol Converted | 37.01 | 0 |
| Wt % 1-Propanol Converted | 0 | 46.3 |
| Wt % Selectivity of Products (Water-Free) | | |
| n-$C_3H_7OH$ | 16.13 | 0.00 |
| i-$C_4H_9OH$ | 3.43 | 19.65 |
| n-$C_4H_9OH$ | 0.00 | 0.00 |
| t-$C_4H_9OH$ | 0.00 | 0.00 |
| CO | 41.83 | 33.73 |
| $CO_2$ | 3.72 | 2.76 |
| $CH_4$ | 4.21 | 1.52 |
| $C_2+$ Hydrocarbons | 13.04 | 11.95 |

TABLE 3-continued

| Alcohol Feed | Run 1<br>3.3 MMeOH/EtOH | Run 2<br>3.4 MMeOH/PrOH |
|---|---|---|
| Ethanol | 0 | 10.2 |
| Acetaldehyde | 10.09 | 0.00 |
| Methyl Formate | 0.00 | 0.00 |
| Crotonaldehyde | 0.00 | 0.00 |
| Methyl Acetate | 0.00 | 0.00 |
| Ethyl Acetate | 0.00 | 0.00 |
| 1-Pentanol | 0.00 | 0.00 |
| Hexanol+ | 0.00 | 0.00 |
| Other | 7.27 | 20.23 |

As can be seen by comparing the product distributions presented in Table 3 with those in Table 1, Catalyst C was less effective for the synthesis of isobutanol than was the non-impregnated KL zeolite Catalyst A despite the fact that the Runs were conducted at the relatively high weight hourly space velocity of about 4.

EXAMPLE 4

This example demonstrates the synthesis of isobutanol from a methanol/ethanol feedstocks using platinum-impregnated Catalyst D. In Run 1, a 3.3M:1M methanol/ethanol feedstock was reacted over 3.23 grams of non-calcined Catalyst D and about 27 cubic centimeters of charcoal. A hydrogen carrier gas was used to provide flow through a quartz-lined reactor. The experimental conditions and product distribution are summarized in Table 4.

TABLE 4

| Alcohol Feed | 3.3 m MeOH/EtOH |
|---|---|
| Temperature, Centigrade | 398 |
| Pressure, Psig | 565 |
| MeOH/EtOH (cc/hr) | 6.05 |
| WHSV (g Alc./g cat/hr) | 1.48 |
| Wt % Methanol Converted | 68.09 |
| Wt % Ethanol Converted | 57.39 |
| Wt % Selectivity of Products (Water-Free) | |
| $n$-$C_3H_7OH$ | 5.14 |
| $i$-$C_4H_9OH$ | 0.82 |
| $n$-$C_4H_9OH$ | 2.83 |
| $t$-$C_4H_9OH$ | 0.00 |
| CO | 63.70 |
| $CO_2$ | 16.20 |
| $CH_4$ | 2.45 |
| $C_2$+ Hydrocarbons | 2.87 |
| Acetaldehyde | 3.61 |
| Methyl Formate | 0.00 |
| Isopropanol | 0.00 |
| Methyl Acetate | 0.00 |
| Ethyl Acetate | 0.00 |
| 1-Pentanol | 0.00 |
| Hexanol+ | 0.00 |
| Other | 2.38 |

As can be seen by comparing the product distributions presented in Table 4 with those in Table 1, Catalyst D was less effective for the synthesis of isobutanol than was the non-impregnated KL zeolite Catalyst A.

The foregoing discussion and Examples are exemplary only, and the invention is not intended to be limited except by the following claims.

We claim:

1. A process for producing a higher molecular weight alcohol from a lower molecular weight feedstock comprising reacting a first linear primary alcohol having X carbon atoms with a second linear primary alcohol having Y carbon atoms over a cation-containing L-type zeolite catalyst at a temperature between 200° and 500° C., at a pressure from subambient to 2,000 psig, and at a weight hourly space velocity between 0.2 and 300 hr$^{-1}$ to produce a product alcohol having X+Y carbon atoms, where X and Y are integers equal to or less than 20.

2. The process of claim 1 wherein the catalyst is selected from the group consisting of alkali, alkaline earth, hydronium or ammonium cation-exchanged L-type zeolites.

3. The process of claim 2 wherein the catalyst has between 1 and 5 weight percent of one or more metals selected from Groups VIII and IB deposited thereon.

4. The process of claim 1 wherein the first alcohol is n-propanol, the second alcohol is methanol, and wherein a product alcohol is isobutanol.

5. The process of claim 1 wherein the first alcohol is n-butanol, the second alcohol is methanol, and a product alcohol is isoamyl alcohol.

6. The process of claim 1 wherein the process is performed at a weight hourly space velocity greater than 1.5 grams of alcohol feedstock per gram of catalyst per hour and wherein the weight percent selectivity for a branched-chain primary alcohol having X+Y carbon atoms is at least 25 percent.

7. A process for producing a higher molecular weight alcohol from a lower molecular weight feedstock comprising reacting a first linear primary alcohol having X carbon atoms and a second linear primary alcohol having Y carbon atoms over a KL zeolite catalyst at a temperature between 200° and 500° C., at a pressure from subambient to 2,000 psig, and at a weight hourly space velocity between 0.2 and 300 hr$^{-1}$ to produce a product alcohol having X+Y carbon atoms, where X and Y are integers less than or equal to 20.

8. The process of claim 7 wherein the first alcohol is a linear primary alcohol having between 1 and 4 carbon atoms, the second alcohol is a linear primary alcohol having between 2 and 4 carbon atoms, and wherein the product alcohol is a branched-chain primary alcohol having X+Y carbon atoms.

9. The process of claim 8 wherein the first alcohol is n-propanol, the second alcohol is methanol, and a product alcohol is isobutanol.

10. The process of claim 8 wherein the first and second alcohols are selected from the group consisting of n-propanol and ethanol or n-butanol and methanol and wherein a product alcohol is isoamyl alcohol.

11. The process of claim 7 wherein the process is performed at a weight hourly space velocity greater than 1.5 grams of alcohol feedstock per gram of catalyst per hour and wherein the weight percent selectivity for a branched-chain primary alcohol having X+Y carbon atoms is at least 25 percent.

12. The process of claim 7 wherein the feedstock further includes between 0 and 10 weight percent of feedstock selected from the group consisting of aldehydes and olefins.

13. A process for making ether fuel components comprising the steps of:
- contacting a first alcohol having X carbon atoms and a second alcohol having Y carbon atoms over a cation-containing L-type zeolite catalyst at a temperature between 200° and 500° C., at a pressure from subambient to 2,000 psig, and at a weight hourly space velocity between 0.2 and 300 hr$^{-1}$ to produce a branched-chain product alcohol having X+Y carbon atoms wherein X+Y is equal to 6 or less;
- dehydrating the alcohol to form an olefin by dehydrating the alcohol in a 20 to 95 percent solution of a mineral acid or by dehydrating vaporized alcohol over a catalyst selected from the group consisting of alumina and solid acid catalysts at a temperature from about the boiling point of the alcohol to about 400° C.; and
- conducting a vapor phase reaction between the olefin and a third alcohol having Z carbon atoms wherein Z can be 1, 2 or 3 to form a dialkyl ether of the form $R_1OR_2$ wherein $R_1$ is an alkyl group having X+Y carbon atoms and wherein $R_2$ is an alkyl group having Z carbon atoms, said reaction occurring over a catalyst selected from the group consisting of medium pore zeolites and acid catalysts.

14. The process of claim 13 wherein the catalyst is a KL zeolite.

15. The process of claim 13 wherein the first alcohol is 1-propanol, the second alcohol is methanol, a product alcohol is isobutanol, the third alcohol is methanol, and the ether is methyl tertiary butyl ether.

16. The process of claim 15 wherein the catalyst is a KL zeolite.

17. The process of claim 13 wherein the first and second alcohols are contacted over the L-type zeolite at a weight hourly space velocity greater than 1.5 grams of alcohol feedstock per gram of catalyst per hour and wherein the weight percent selectivity for a branched-chain primary alcohol having X+Y carbon atoms is at least 25 percent.

* * * * *